(12) United States Patent
Kerr

(10) Patent No.: US 6,743,241 B2
(45) Date of Patent: Jun. 1, 2004

(54) LAPAROSCOPIC PORT SITE FASCIAL CLOSURE DEVICE

(75) Inventor: Stephen Kerr, Manhattan Beach, CA (US)

(73) Assignee: Intellimed Surgical Solutions LLC, San Juan Capistrano, CA (US)

( * ) Notice: Subject to any disclaimer, the term of this patent is extended or adjusted under 35 U.S.C. 154(b) by 0 days.

(21) Appl. No.: 10/086,318

(22) Filed: Mar. 1, 2002

(65) Prior Publication Data

US 2003/0167063 A1 Sep. 4, 2003

(51) Int. Cl.⁷ ................................................ A61B 17/04
(52) U.S. Cl. ........................................ 606/144; 606/139
(58) Field of Search ........................... 606/148, 144, 606/145, 139

(56) References Cited

U.S. PATENT DOCUMENTS

| | | |
|---|---|---|
| 5,320,632 A | 6/1994 | Heidmueller |
| 5,364,408 A | 11/1994 | Gordon |
| 5,368,601 A | 11/1994 | Sauer et al. |
| 5,374,275 A | 12/1994 | Bradley et al. |
| 5,403,329 A | 4/1995 | Hinchcliffe |
| 5,458,609 A | 10/1995 | Gordon et al. |
| 5,476,469 A | 12/1995 | Hathaway et al. |
| 5,478,353 A | 12/1995 | Yoon |
| 5,507,757 A | 4/1996 | Sauer et al. |
| 5,700,272 A | 12/1997 | Gordon et al. |
| 5,741,277 A | 4/1998 | Gordon et al. |
| 5,741,279 A | 4/1998 | Gordon et al. |
| 5,860,991 A | 1/1999 | Klein et al. |
| 5,868,762 A * | 2/1999 | Cragg et al. ................ 606/144 |
| 5,954,734 A | 9/1999 | Thomason et al. |
| 5,964,773 A | 10/1999 | Greenstein |
| 6,117,144 A | 9/2000 | Nobles et al. |
| 6,183,485 B1 | 2/2001 | Thomason et al. |
| 6,355,050 B1 * | 3/2002 | Andreas et al. ............. 606/144 |

FOREIGN PATENT DOCUMENTS

| | | |
|---|---|---|
| DE | 4211459 | 10/1993 |
| EP | 302304 A | 2/1989 |
| EP | 686662 B1 | 12/1995 |
| WO | WO 02/067273 A1 | 2/2002 |

* cited by examiner

Primary Examiner—Michael J. Milano
Assistant Examiner—Bradford C Pantuck
(74) Attorney, Agent, or Firm—Raymond A. Miller; Pepper Hamilton LLP

(57) ABSTRACT

A laparoscopic fascial closure device for fashioning a secure closure about a laparoscopic puncture site. The device comprises an elongate cannula having proximal and distal ends. A needle suture complex is selectively deployed from the distal end of the device that is operative to deploy a suture across the puncture site from within the body and draw the free ends of the suture outwardly from the body via the laparoscopic port site. The device is configured to be utilized through a ten millimeter or larger laparoscopic port, and is operative to position the suture at the puncture site such that the suture extends in a diametrically-opposed configuration at least 1.0 cm or greater across opposed sides of the puncture site.

12 Claims, 4 Drawing Sheets

LAPAROSCOPIC PORT SITE FASCIAL CLOSURE DEVICE

BACKGROUND OF THE INVENTION

Laparoscopic surgery is a well-known, widely utilized surgical technique that advantageously reduces patient recovery time due to its minimal tissue damage, which consequently permits the patient to return to normal activity in a shorter period of time. Generally, laparoscopic surgery relies upon the formation of one or more trocar puncture wounds through which are deployed surgical instruments and a rod-like telescope with a light source to enable the surgeon to view the organs and conduct the surgery.

Notwithstanding the tremendous advantages afforded by laparoscopic surgery, such technique still presents substantial clinical problems. More specifically, the puncture wounds created within the body by the surgeon to gain access to the surgical site are often difficult and time-consuming to close, and can place great demands on the surgeon. Such task is made even more difficult when laparoscopic surgery is performed upon obese patients where there is a relatively deep puncture wound formed through a relatively small puncture site or incision. Indeed, the puncture site frequently needs to be enlarged following the laparoscopic procedure to ensure that the site is closed at the interior abdominal wall. Ironically, the need to enlarge the puncture site in order to adequately close the same partially negates the primary advantages of laparoscopic surgery; however, such practice is essential insofar as failure to properly close the puncture wound can lead to serious medical complications.

To address such shortcomings, numerous attempts have been made to develop instruments capable of quickly and effectively forming a closure of a laparoscopic fascial defect or puncture site. Exemplary of such attempts include those devices disclosed in U.S. Pat. No. 5,741,279, issued to Gordon et al., on Apr. 21, 1998, entitled ENDOSCOPIC SUTURE SYSTEM; U.S. Pat. No. 5,374,275, issued to Bradley et al., on Dec. 20, 1994, entitled SURGICAL SUTURING DEVICE AND METHOD OF USE; U.S. Pat. No. 5,964,773, issued to Greenstein on Oct. 12, 1999, entitled LAPAROSCOPIC SUTURING DEVICE AND SUTURE NEEDLES; U.S. Pat. No. 5,403,329, issued to Hinchcliffe on Apr. 4, 1995; and U.S. Pat. No. 5,507,757, issued to Sauer et al. on Apr. 16, 1996, entitled METHOD OF CLOSING PUNCTURE WOUNDS, the teachings of all of which are expressly incorporated herein by reference.

Such attempts, however, have proven less than satisfactory and fail to provide a practical solution to the foregoing problems. In this regard, substantially all such devices allegedly designed to facilitate the closure of a laparoscopic puncture site are incapable of deploying a suture a sufficient distance about the puncture site to fashion an appropriate closure. In this respect, prior art devices, such as those referenced above, are operative to stitch a suture into position at points diametrically across the puncture site; however, such suture typically only extends thereacross by a limited distance, which is less than 1.0 cm. Such limited distance fails to sufficiently approximate the peritoneum and fascia surrounding the puncture site sufficiently to form an adequate closure. While it is recognized that a suture extending a greater distance across the puncture site would be more advantageous, the capability of prior art devices position such a suture have not heretofore been available insofar as any laparoscopic fascial closure device must necessarily be insertable through a 10 mm laparoscopic port, which places considerable spacial constraints on the design of such devices.

Additionally disadvantageous with such prior art closure devices include the failure of such devices to selectively deploy needles for positioning and stitching a suture across the puncture site that can ultimately be withdrawn from the puncture wound without the need to enlarge the incision or puncture site. Among those devices possessing such defect include those disclosed in U.S. Pat. Nos. 5,964,733 and 5,403,329, referenced above, which deploy needles that, after having been deployed to fix a suture in position across an intra-abdominal puncture site, are inoperative to become repositioned within the device deployed thereby to thus atraumatically withdraw such needles from the patient.

Accordingly, there is a substantial need in the art for a laparoscopic fascial closure device that overcomes the aforementioned shortcomings in the art. Specifically, there is a need for such a device that is capable of being deployed through a 10 mm or larger laparoscopic port or puncture site that is further capable of deploying a suture at least 1.0 cm across from the periphery thereof. There is additionally a need for such a device that is capable of deploying a suture across a laparoscopic puncture site that provides for the retraction and capture of needles utilized to secure such suture in position back within the device deployed thereby to thus enable the needles to be easily and atraumatically withdrawn from the laparoscopic puncture wound.

BRIEF SUMMARY OF THE INVENTION

The present invention specifically addresses and alleviates the above-identified deficiencies in the art. More specifically, the present invention is directed to a laparoscopic fascial closure device that is operative to fashion a secure closure of laparoscopic puncture wounds, and in particular, in abdominal tissues. According to a preferred embodiment, the device comprises an elongate cannula or other hollow tubular member having proximal and distal ends, the latter being configured to be inserted within the body via the laparoscopic trocar-created punctures used to perform the laparoscopic procedure. To that end, the cannula is sized to be inserted through a puncture site of at least 10 mm or greater.

Disposed within the cannula, and more particularly the distal end thereof, is a needle/suture complex consisting of two diametrically-opposed needle members having an elongate suture extending therebetween that are operatively transitional from a first insertion configuration, whereby the needles are confined within the distal-most end of the cannula for insertion through the abdomen to the puncture site; a second operative configuration whereby the needle members extend outwardly from the distal-most end of the cannula such that each respective needle is oriented toward the fascia surrounding the puncture site in a generally perpendicular orientation. Such needle members, according to said second configuration, are further oriented to extend outwardly from the distal-most end of the cannula by a distance of at least 1.0 cm or greater and pierce through the peritoneum and fascia at diametrically opposed points across the puncture site. To facilitate the ability of the needle/suture complex to gather tissue about a puncture site to form the desired closure, the needle/suture complex will preferably be positioned upon a tapered mount having a generally hourglass shape to thus enable tissue to gather thereabout.

The needle members are further operative to assume a third retraction configuration whereby each respective tip of the two diametrically-opposed needles are brought into and contained within the distal end of the cannula. To facilitate the ability of the device to assume the third configuration, a grasping mechanism is disposed within the cannula that is operative to grasp each respective needle tip and draw the same back into the cannula. The needle/suture complex is mounted upon a connecting rod disposed within the cannula, which is operative to be advanced downwardly into the cannula such that the needles of the needle/suture complex are deployed through and ultimately retracted back within the lumen of the cannula. When in such third configuration, the device is then withdrawn from the body.

In use, the suture connected across the respective needles is caused to extend across the puncture site with the free ends thereof being drawn upwardly from the puncture wound as the device is withdrawn from the body, which thus leaves the two ends of the sutures free to be cut away from the needles and then tied down to close the fascial defect. Advantageously, because the suture is positioned such that the same extends at least 1.0 cm or greater across opposed sides of the puncture site, a sufficient amount of tissue is utilized to give strength to the closure. Additionally, such design advantageously eliminates the need to deploy additional sutures across the suture site, as is necessary with prior art needle passing devices which must be passed multiple times across the puncture wound site. The device further forms a closure in such a manner that the pneumoperitoneum is maintained, thus enabling the device to be utilized without direct visualization with a laparoscope.

It is therefore an object of the present invention to provide a laparoscopic port site fascial closure device that is substantially more effective and efficient at forming a closure about a laparoscopic puncture site than prior art devices and techniques.

Another object of the present invention is to provide a laparoscopic port site fascial closure device that is capable of forming a closure about a laparoscopic puncture site utilizing a single deployment thereof.

Another object of the present invention is to provide a laparoscopic port site fascial closure device that can form a closure about a laparoscopic puncture site in a manner that is far less traumatic than prior art devices and techniques.

Another object of the present invention is to provide a laparoscopic port site fascial closure device that is able to form a closure about a laparoscopic puncture site such that the pneumoperitoneum is maintained such that the abdominal wall is kept away from the abdominal viscera.

Another object of the present invention is to provide a laparoscopic port site fascial closure device that is capable of being utilized without direct visualization.

Still further objects of the present invention include a laparoscopic port site fascial closure device that can be utilized to form a closure about virtually any type of laparoscopic puncture site that is at least 10 mm or greater, is of simple construction, reliable, and exceedingly simple and time efficient to utilize.

BRIEF DESCRIPTION OF THE DRAWINGS

These, as well as other features of the present invention, will become more apparent upon reference to the drawings wherein.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figures 1, 2:
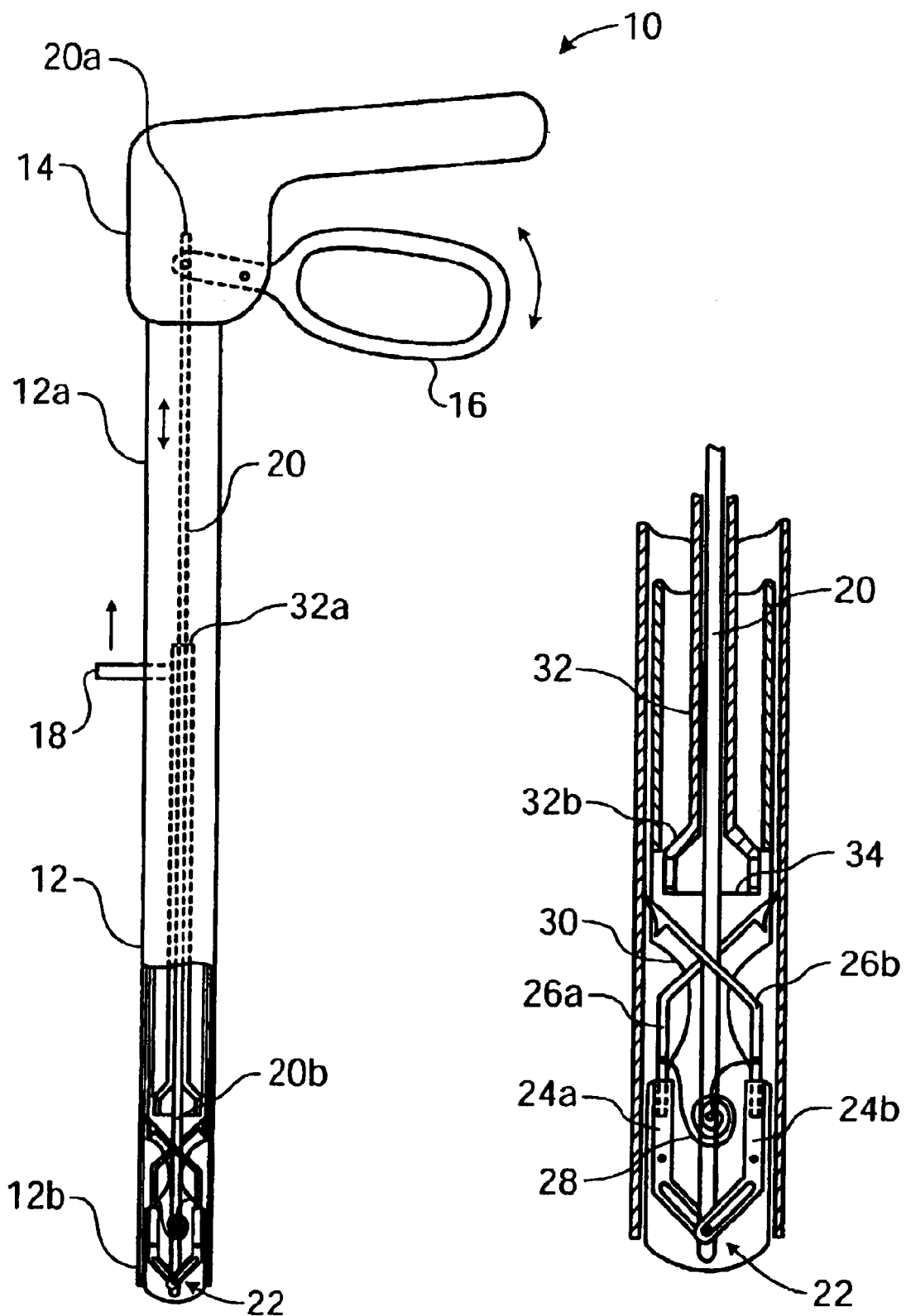
FIG. 1 is a side, partial cross-sectional view of a laparoscopic port site fascial closure device constructed in accordance with a preferred embodiment of the present invention.
FIG. 2 is an expanded cross-sectional view of the distal end of the device depicted in FIG. 1.

Referring now to the Figures, and initially to FIG. 1, there is shown a laparoscopic fascial closure device 10 constructed in accordance with a preferred embodiment of the present invention. As illustrated, the device 10 comprises an elongate cannula member 12 having proximal and distal ends 12a, 12b, with the distal end 12b being operative for insertion into the patient, and the proximal end 12a having a handle 14 and actuation mechanisms 16, 18 to facilitate handling and operation of the device by a surgeon, discussed more fully below.

Axially disposed within the lumen of the cannula 12 is an elongate connecting rod 20 having a proximal end 20a that is secured to a trigger mechanism 16 extending outwardly from the proximal end 12a of the cannula 12. As will be appreciated by those skilled in the art, the trigger mechanism 16 cooperates with the handle 14 formed upon the proximal end 12a of the cannula 12 to thus enable a surgeon to simultaneously grasp and operate the device 10. The distal end 20b of the connecting rod 20 is coupled to a needle/suture complex 22, more clearly seen in FIG. 2, the latter consisting of an opposed pair of angled needle holders 24a, 24b pivotally connected to the connecting rod 20, an opposed pair of angled needles 26a, 26b received within dedicated ones of the needle holders 24a, 24b, and an elongate suture 28 having a first end attached to a respective one of the needles, and the other end attached to the respective other end of the needle. The needle/suture complex 22 will further preferably be positioned upon a tapered mount 30 having a generally hourglass shape to facilitate the ability of the device to form a closure, discussed more fully below, as more clearly seen in FIG. 6.

Additionally provided within the device 10 of the present invention is a needle trap mechanism 32, more clearly depicted in FIG. 2, comprised of an elongate cylindrical sleeve axially mounted about a portion of the connecting rod 20. The needle trap includes a proximal end 32a having a handle or other graspable member formed thereon, shown as 18 in FIG. 1, the latter extending partially from the cannula member 12 to thus enable a surgeon to manipulate the same. Formed upon the distal end 32b of the needle trap is a generally bell-shaped or frusto-conical shaped housing 34 operative to grasp the tips of the opposed needles 26a, 26b and ultimately contain the same therewithin such that the needles 26a, 26b may ultimately be pulled from their respective needle holders 24a, 24b within which they are received following deployment of the device 10 and contained within the cannula 12, as discussed more fully below.

The device 10 of the present invention is specifically configured to be deployed through laparoscopic ports of at least 10 mm or greater. As will be recognized by those skilled in the art, although certain laparoscopic procedures are performed utilizing laparoscopic ports of less than 10 mm, by far the majority of such procedures rely upon at least one or more larger ports having a size of 10 mm or greater. It should be understood, however, that the present invention could be adapted for deployment through smaller laparoscopic ports, as may be necessary in other applications.

Figure 3:
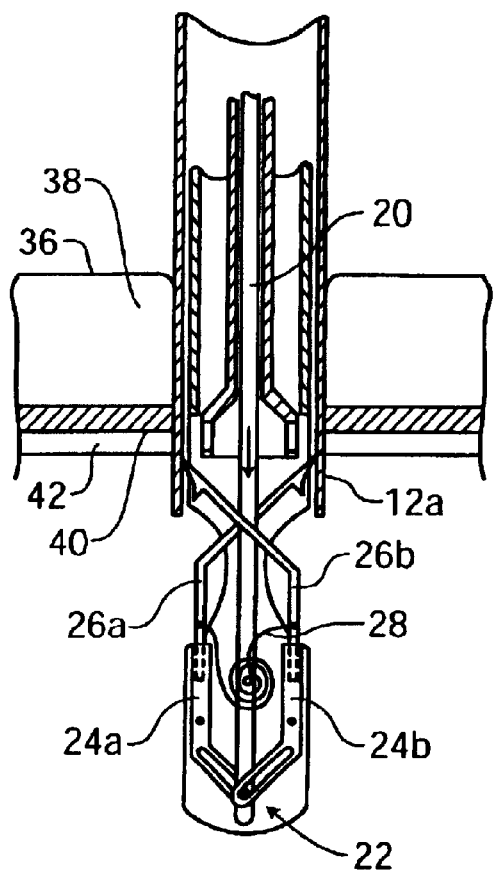
FIG. 3 is a cross-sectional view of the distal-most end of the device depicted in FIG. 2 shown deployed through a laparoscopic puncture wound through the skin, subcutaneous fat, fascia, and peritoneum of a patient.

Referring now to FIG. 3, there is shown the distal end of the device 10 depicted in FIGS. 1–2 shown deployed through the distal end of a laparoscopic port and within the abdominal cavity of a patient. As discussed above, the distal end of the device 10 will be inserted through a laparoscopic port. The formation of laparoscopic ports is well-known in the arts and utilized extensively in the practice of laparoscopic surgery. Briefly, such ports are formed via the use of trocars followed by the placement of a port into the patient, the latter defining a channel through which surgical instruments and laparoscopes are deployed for a given surgical procedure. The device 10 of the present invention is specifically used following the surgical procedure to form a closure about the puncture site within the body through which the port was utilized.

Initially, the distal end of the device 10 is inserted through the port such that the distal-most end of the device 10 extends into the abdominal cavity through layers of skin 36, subcutaneous fat 38, fascia 40, and peritoneum 42. The connecting rod 20 is then actuated via the trigger (not shown) such that the connecting rod 20 extends downwardly through the distal end 12b of the cannula 12 such that the needle/suture complex 22 is caused to extend therefrom. As illustrated, the needle/suture complex 22 will be deployed within the abdominal cavity, and beneath the skin 36, subcutaneous fat 38, fascia 40 and peritoneal 42 layers through which the port extends.

Figure 4:
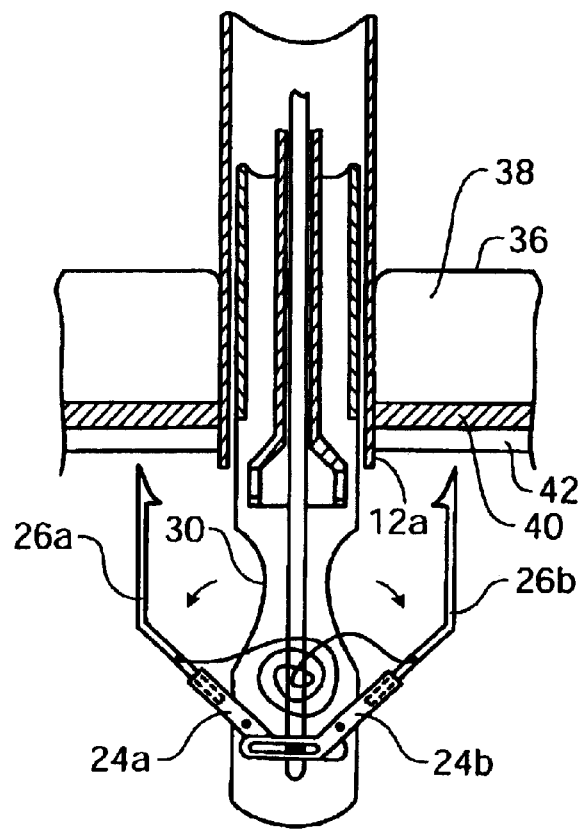
FIG. 4 is a cross-sectional view of the distal end of the device depicted in FIGS. 2–3 depicting a needle suture complex being deployed through the distal-most end thereof, the needle suture complex assuming an operative configuration for stitching a suture across the puncture site formed within the fascia and peritoneum.

Once the needle/suture complex 22 is caused to extend through the distal-most end 12b of the cannula 12, the needle/suture complex 22 transitions from its first, folded configuration depicted in FIGS. 2–3 to a second operative configuration, as illustrated in FIG. 4. In such operative configuration, the needle holder arms 24a, 24b pivot outwardly such that the needles 26a, 26b held thereby spread out and extend away from the distal opening of the cannula 12a. To achieve that end, it is contemplated that the needle holder arms 24a, 24b may be outwardly biased via the use of springs or some other biasing force. As illustrated, the needle holder arms 24a, 24b and needles 26a, 26b held thereby are formed to have bends therein to thus enable the needles 26a, 26b to achive an orientation whereby the needles are positioned in a perpendicular fashion relative the peritoneum 42 and fascia 40, and generally parallel to the cannula 12 of the device 10. The arms 24a, 24b and needles 26a, 26b are further configured such that the same extend in diametrically opposed directions and, importantly, extend from the distal-most end of the cannula 12, and hence the laparoscopic port opening or puncture site, by a distance of at least 1.0 cm or greater.

In this respect, one of the chief advantages of the operation of the device 10 of the present invention is the ability of the same to ultimately stitch a suture into position a sufficient distance about the port opening to thus cause a more secure closure to ultimately be formed. Prior art devices, in contrast, are incapable of delivering a suture sufficiently across a laparoscopic puncture wound site to fashion a desired secure closure within the abdominal cavity.

Figures 5, 6:
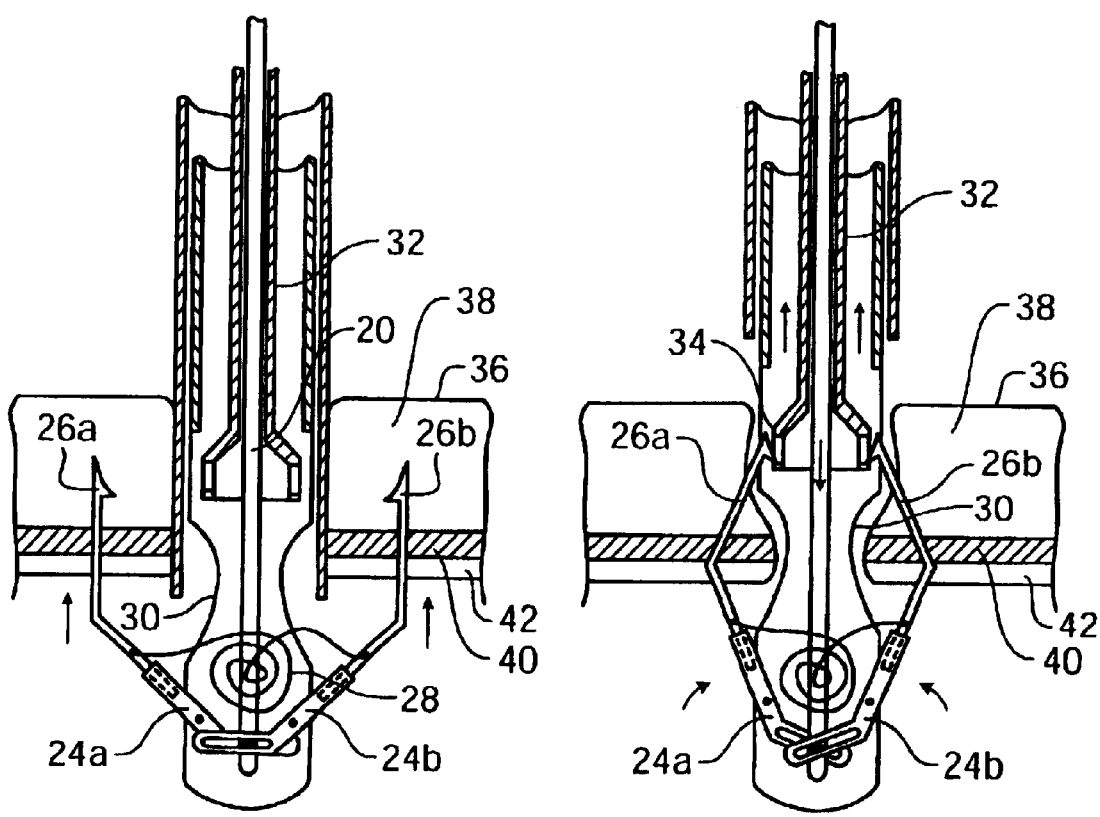
FIG. 5 is a cross-sectional view of the device depicted in FIGS. 2–4 showing the needle/suture complex extending upwardly into the peritoneum, fascia and subcutaneous fat layers.
FIG. 6 is a cross-sectional view of the device depicted in FIGS. 2–5, whereby the needles of the needle/suture structure are shown being captured within the distal end of the device.

To that end, there is shown in FIG. 5 the process by which the suture 28, as deployed by the needle/suture complex 22, is positioned across the laparoscopic puncture site. The opposed needles 26a, 26b extend upwardly and penetrate the peritoneum 42 and fascia 40 in a generally perpendicular fashion and are operative to traverse the peritoneum 42, subcutaneous fat 38 and fascia 40 prior to being captured within the lumen of the cannula 12, discussed more fully below. As will be appreciated, such pathway of penetration defined by the opposed needles 26a, 26b provide for substantially more secure suture placement. To facilitate the ability of the device 10 to form a closure of the puncture site via placement of the suture 28, tapered mount 30 upon which the needle/suture complex 22 is positioned enables tissue to be gathered radially thereabout.

In order to safely and atraumatically withdraw the needles 26a, 26b deploying the suture 28 about the puncture site, there is further shown in FIG. 6 a mechanism by which the present invention operates to accomplish same. As illustrated, the needle/suture complex 22 is operative to assume a third retraction configuration whereby the tips of the respective needles 26a, 26b are captured by the needle trap mechanism 32, and ultimately caused to detach from the respective needle holders 24a, 24b and remain contained within the cannula 12 of the device 10. Specifically, as the connecting rod 20 is pushed downwardly, the needle holder arms 24a, 24b are forced to rotate inwardly. Such motion consequently causes the needle tips of the opposed needles 26a, 26b to likewise rotate inwardly, such that the tips are received within the capture area 34 formed upon the distal-most end of the needle trap mechanism 32 positioned axially about the connecting rod 20. Once captured, the needle trap mechanism 32, with needle tips captured thereby, is pulled upwardly through the cannula 12 via a lever (i.e., lever 18 in FIG. 2) formed on the proximal end thereof extending from the cannula 12 such that each respective needle 26a, 26b is caused to dislodge from the needle holder arm 24a, 24b that it had respectively engaged. As a consequence, the needles 26a, 26b become disengaged from the needle suture complex 22 and are ultimately contained safely within the lumen of the cannula 12.

Figures 7, 8:
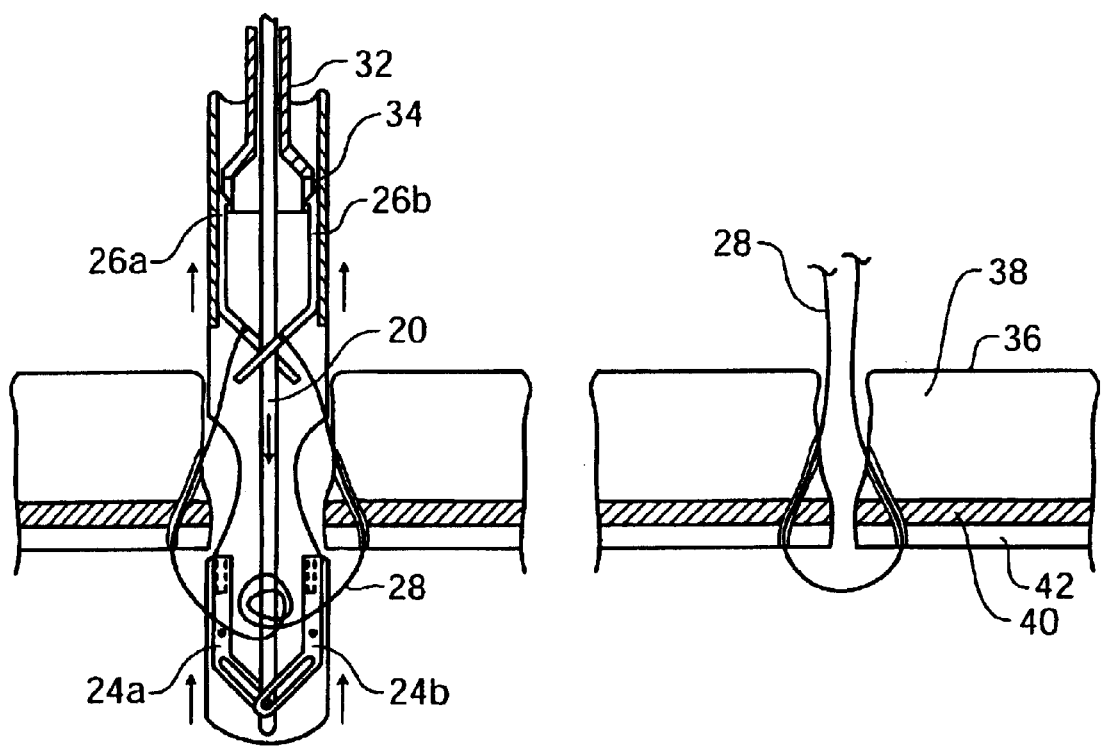
FIG. 7 is a cross-sectional view of the device depicted in FIGS. 2–6 wherein the needles of the needle/suture complex are captured entirely within the distal end of the device as the device is shown being pulled upwardly from the laparoscopic puncture wound such that the suture of the needle/suture complex remains fixed in position across the laparoscopic puncture site formed within the fascia and peritoneum.
FIG. 8 is a cross-sectional view depicting the placement of the suture following withdrawal of the laparoscopic fascial closure device from the patient's body.

As illustrated in FIG. 7, as a result of the removal of the needles 26a, 26b from the needle holder arms 24a, 24b, the needles 26a, 26b are caused to advance upwardly through the cannula 12 with the suture ends remaining attached thereto. As will be readily appreciated, by virtue of having been stitched across opposed sides of the laparoscopic port or puncture site, the suture 28 will extend thereacross and upwardly through the piercings made by the respective needles 26a, 26b through the peritoneum 42, fascia 40, fatty tissue 38 and ultimately through the previously formed laparoscopic port channel. As will be appreciated, such suture 28 will be pulled through the body by merely withdrawing the entire device 10 from the patient, as shown in FIG. 6.

Ultimately, the suture 28 will be positioned across the laparoscopic puncture site in the manner depicted in FIG. 8. As illustrated, the respective ends of the suture 28 will extend outwardly from the body but around the puncture site to thus fashion a closure of the site. To that end, the suture 28 may be manipulated according to a variety of techniques to thus ensure that the puncture site remains closed thereby.

Additional modifications and improvements of the present invention may also be apparent to those of ordinary skill in the art. For example, it is contemplated that a variety of mechanisms exist that are capable of capturing needle tips of the needles deployed by the needle/suture complex 22 of the present invention. Additionally, it is contemplated that a variety of needle and needle/holder configurations may be derived that are capable of causing the needles to ultimately penetrate through the peritoneum, fascia and fatty tissue, in a generally perpendicular orientation, and further are caused to advance through such tissues at a distance of 1.0 cm or greater from the periphery of the puncture site sought to be closed. Moreover, a variety of mechanisms may be utilized to deploy the needle/suture complex, which may include a connecting rod configured to retract, twisted or otherwise manipulated to cause the needle/suture complex to transition to its various operative configurations. Thus, the particular combination of parts and steps described and illustrated herein is intended to represent only certain embodiments of the present invention, and is not intended to serve as limitations of alternative devices and methods within the spirit and scope of the invention.

What is claimed is:

1. A laparoscopic fascial closure device for fashioning a closure of a laparoscopic puncture site comprising:
   a. an elongate, hollow cannula member having a proximal and distal ends;
   b. an elongate connecting rod disposed axially within said cannula, said connecting rod having a proximal end orientated towards said proximal end of said cannula and a distal end orientated toward said distal end of said cannula, said connecting rod having a trigger formed upon the proximal end thereof operative to selectively cause said connecting rod to advance distally or retract proximally within said cannula;
   c. a needle/suture complex mounted upon said distal end of said connecting rod, said needle/suture complex comprising at least one pair of needles having a suture extending therebetween, said needles being operatively transitional between:
      (i) a first folded configuration wherein said needles are operative to extend through the lumen of said cannula;
      (ii) a second operative configuration wherein said needles extend in opposed directions from the distal end of said cannula such that each respective needle extends a distance from the periphery of said puncture site; and
      (iii) a third retracted configuration wherein said needles are biased inwardly toward the lumen of said cannula, independent of the needles' shape;
   d. a needle trap mechanism disposed within the lumen of said cannula and operative to lockingly engage with said needles of said needle/suture complex after said needles assume said third operative configuration; and
   e. wherein said needle trap mechanism is operative to draw said needles into the lumen of said cannula such that the device may be withdrawn from the body with the suture extending between the needles, forming a closure of said laparoscopic puncture site.

2. The device of claim 1 wherein said distal end of said cannula is positionable through a laparoscopic port having a size of 10 nm or greater.

3. The device of claim 1 wherein said needle suture complex further comprises at least one pair of needle holder arms, each respective one of said at least one pair of said needle holder arms being operative to receive a respective one of said pair of needles.

4. The device of claim 3 wherein said respective one of said pair of needles is operative to disengage from said needle holder arms as said needle/suture complex transitions from its second operative configuration to its third operative configuration.

5. The device of claim 3 wherein each respective one of said pair of needle holder arms are biased to extend in diametrically opposed directions across said puncture site as said needle holder arms assume said second operative configuration.

6. The device of claim 1 wherein each respective one of said pair of needles are biased to extend in diametrically opposed directions across said puncture site as said needle/suture complex assumes said second operative configuration.

7. The device of claim 1 further comprising a handle formed on the proximal end of said cannula.

8. The device of claim 7 wherein said handle and said trigger are positioned relative one another to enable the handle to be grasped and the trigger to be manipulated by a single hand of a user.

9. The device of claim 1 where said needle trap mechanism comprises an elongate cylindrical sleeve axially mounted about said connecting rod within said cannula, said needle trap mechanism having a proximal end with a lever formed thereon, extending from said cannula, and a bell-shaped distal end having a needle catch formed therein, said needle catch being operative to lockingly engage with needle tips of said needle/suture complex when said complex assumes said third operative configuration.

10. The device of claim 9 wherein said lever formed upon said needle trap mechanism is operative to cause said needle trap mechanism to extend distally and retract proximally within the said cannula.

11. The device of claim 10 wherein said needle trap mechanism, when lockingly engaged with said needle tips of said needles, captures said needles within said cannula when said needle trap mechanism retracts proximally within said cannula.

12. The device of claim 1 further comprising a tapered mount formed upon said distal end of said connecting rod and holding said needle/suture complex, said tapered mount having a generally hourglass shape.

* * * * *